(12) United States Patent
Ye et al.

(10) Patent No.: US 11,630,242 B1
(45) Date of Patent: Apr. 18, 2023

(54) POLYPHENYL THIOETHER (AND SYNTHESIS PATH) FOR USE IN LIQUID LENSES

(71) Applicant: META PLATFORMS TECHNOLOGIES, LLC, Menlo Park, CA (US)

(72) Inventors: Sheng Ye, Redmond, WA (US); Lafe Purvis, Redmond, WA (US); Andrew John Ouderkirk, Kirkland, WA (US); Manuel Caraballo-Sánchez, Extremadura (ES); Hayden Erik Hernández, Oxford (GB)

(73) Assignee: Meta Platforms Technologies, LLC, Menlo Park, CA (US)

( * ) Notice: Subject to any disclaimer, the term of this patent is extended or adjusted under 35 U.S.C. 154(b) by 379 days.

(21) Appl. No.: 17/082,059

(22) Filed: Oct. 28, 2020

Related U.S. Application Data (60) Provisional application No. 62/941,618, filed on Nov. 27, 2019.

(51) Int. Cl.
*G02B 1/06* (2006.01)
*G02B 3/14* (2006.01)
*C07C 319/12* (2006.01)

(52) U.S. Cl.
CPC .............. *G02B 1/06* (2013.01); *C07C 319/12* (2013.01); *G02B 3/14* (2013.01)

(58) Field of Classification Search
CPC ........ C12N 2501/115; C12N 2501/119; C12N 2501/125; C12N 2501/15; C12N 2501/155; C12N 2501/235; C12N 5/062; C12N 5/0696
See application file for complete search history.

(56) References Cited

U.S. PATENT DOCUMENTS

| | | | |
|---|---|---|---|
| 7,256,943 B1 | 8/2007 | Kobrin et al. | |
| 8,018,658 B2 * | 9/2011 | Lo | G02B 3/14 359/886 |
| 2019/0169157 A1 | 6/2019 | Oehrlein et al. | |

\* cited by examiner

*Primary Examiner* — Joseph P Martinez
*Assistant Examiner* — Vipin Patel
(74) *Attorney, Agent, or Firm* — Greenberg Traurig, LLP (57) ABSTRACT

A liquid lens fluid composition includes a polyphenyl ether molecule having from 2 to 7 aromatic rings, where the rings include ortho substitutions, meta substitutions, or a combination of ortho, meta, and para substitutions. Inter-ring linkages may include sulfur or oxygen. The liquid lens fluid composition may be characterized by a refractive index over the visible spectrum of at least 1.4, a viscosity at room temperature of less than approximately 1000 cP, and a freezing point of less than approximately −10° C.

20 Claims, 9 Drawing Sheets

FIG. 19 ined States Patent

POLYPHENYL THIOETHER (AND SYNTHESIS PATH) FOR USE IN LIQUID LENSES

CROSS REFERENCE TO RELATED APPLICATION

This application claims the benefit of priority under 35 U.S.C. § 119(e) of U.S. Provisional Application No. 62/941,618, filed Nov. 27, 2019, the contents of which are incorporated herein by reference in their entirety.

BRIEF DESCRIPTION OF THE DRAWINGS

The accompanying drawings illustrate a number of exemplary embodiments and are a part of the specification. Together with the following description, these drawings demonstrate and explain various principles of the present disclosure.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the present disclosure covers all modifications, equivalents, and alternatives falling within the scope of the appended claims.

DETAILED DESCRIPTION OF EXEMPLARY EMBODIMENTS

Liquid lenses can be used to enhance imaging system flexibility across a wide variety of applications that benefit from rapid focusing. For instance, by integrating an actuatable liquid lens, an imaging system can rapidly change the plane of focus to provide a sharper image, independent of an object's distance from the lens. The use of liquid lenses may be particularly advantageous for applications that involve focusing at multiple distances, where objects under inspection may have different sizes or may be located at varying distances from the lens, such as package sorting, barcode reading, security, and rapid automation, in addition to virtual reality/augmented reality devices. In artificial reality devices, the implementation of liquid lenses is typically constrained by their thickness, weight, and the capabilities of their actuation systems and power supplies.

In some example liquid lens architectures, a fixed volume of liquid may be disposed between a rigid lens or substrate and a thin, transparent elastic membrane. In further liquid lens architectures, the enclosed volume of liquid may be increased or decreased during operation of the lens. In each of the foregoing approaches, by moving the elastic membrane the liquid within the lens assembly may be redistributed such that the curvature of the elastic membrane is changed. The changed curvature of the lens surface can vary the optical power of the lens.

Notwithstanding recent developments, it would be advantageous to provide a transparent, low viscosity, and non-toxic fluid suitable for incorporation into a liquid lens. Throughout the instant specification, unless the context clearly indicates otherwise, the term "liquid" may be used interchangeably with the term "fluid."

The present disclosure relates to a class of polyphenyl ethers capable of being used as the lens fluid in a liquid lens. Polyphenyl ethers are compounds that include from 2 to 7 phenyl groups (aromatic rings) that are bonded (linked) to one another via a sulfur atom or an oxygen atom. A "phenyl group" (or a "phenyl ring") is a group of atoms having the chemical formula $C_6H_5$, and may be regarded as a benzene ring missing a hydrogen atom that may be substituted by a functional group, whereas a "phenylene group" (or a "phenylene ring") is a di-substituted benzene ring (arylene) having the chemical formula $C_6H_4$.

According to various embodiments, polyphenyl ethers including polyphenyl thioethers may be characterized by a high refractive index, low viscosity, and low toxicity, enabling the production of a liquid lens for AR/VR systems that is thin, light, and comfortable to wear. In various aspects, a sulfur atom may be more polarizable than an oxygen atom and, as such, a thioether may typically have a higher refractive index and a lower viscosity than the corresponding ether.

A layer or material that is "transparent" or "optically transparent" may, in some examples, be characterized by a transmissivity within the visible spectrum of at least approximately 90% (e.g., approximately 90%, approximately 95%, approximately 96%, approximately 97%, approximately 98%, approximately 99%, approximately 99.5%, or approximately 99.9%, including ranges between any of the foregoing values) and less than approximately 10% bulk haze.

In some embodiments, a lens fluid having a "high refractive index" may have a refractive index over the visible spectrum of at least approximately 1.4, e.g., approximately 1.4, approximately 1.5, approximately 1.6, or approximately 1.7, approximately 1.8, approximately 1.9, or approximately 2.0, including ranges between any of the foregoing values. In some embodiments, a lens fluid may have a refractive index measured at approximately 589 nm of at least approximately 1.4 over a temperature range extending from approximately −10° C. to approximately 60° C.

The lens fluids disclosed herein may have a low viscosity and a correspondingly high mobility, which may beneficially impact the time needed for the fluid in a lens to accurately and precisely deform a lens surface. A lens fluid having a "low viscosity" may, in some examples, have a viscosity at room temperature (i.e., approximately 25° C.) of less than approximately 1000 centipoise (cP), e.g., approximately 3 cP, approximately 5 cP, approximately 10 cP, approximately 20 cP, approximately 50 cP, approximately 100 cP, approximately 200 cP, approximately 500 cP, or approximately 1000 cP, including ranges between any of the foregoing values. In certain aspects, a lens fluid may have a viscosity of approximately 500 centipoise or less in order to achieve a response time of approximately 100 ms or less while avoiding overshooting the intended deformation. In example embodiments, a polyphenyl thioether-based lens fluid may have a viscosity of less than 1000 cP at room temperature and a freezing point of less than approximately −10° C.

In accordance with some embodiments, the presently-disclosed lens fluids may exhibit stable characteristics (e.g., transparency, viscosity, volume, etc.) over typical operating conditions, including pressures associated with lens actuation and temperatures ranging from approximately −10° C. to approximately 60° C. As used herein, a characteristic that is "stable" may, in certain examples, exhibit a variation of at most 10% (e.g., 1%, 2%, 5%, or 10%, including ranges between any of the foregoing values) over a range of operating conditions, including temperature, pressure, etc. In some examples, a lens fluid may behave as a Newtonian fluid.

In some embodiments, a liquid lens may include a polyphenyl thioether-based lens fluid. Example lens fluids may include a mixture of polyphenyl thioethers and polyphenyl ethers. In further embodiments, a liquid lens may include a polyphenyl thioether-based lens fluid where the lens fluid is substantially free of any polyphenyl ether-based content. That is, example lens fluids may consist essentially of one or more polyphenyl thioether molecules or, in some embodiments, consist of one or more polyphenyl thioether molecules.

The lens fluids disclosed herein may include linear, branched, or star-shaped polyphenyl thioether molecules having from 2 to 7 aromatic rings per molecule, e.g., 2, 3, 4, 5, 6 or 7 aromatic rings. In some aspects, example polyphenyl thioether molecules may be represented by the formula P-S(P'-S)$_n$-P, where P is a phenyl group, P' is a phenylene group, S is sulfur, and n is an integer having a value of from 0 to 5. In further aspects, example polyphenyl ether molecules may be represented by the formula P-X(P'-Y)$_n$-P, where P is a phenyl group, P' is a phenylene group, X and Y may independently be chosen from sulfur and oxygen, and n is an integer having a value of from 0 to 5. In both polyphenyl thioether compositions and polyphenyl ether compositions, the aromatic rings may include all ortho linkages, all meta linkages, ortho and meta linkages, or a combination of ortho, meta, and para linkages.

In some embodiments, one or more of the phenyl or phenylene groups may be substituted with an aliphatic group or a halogen element, such as chlorine, bromine, or iodine. Aliphatic-substituted phenyl group(s) and aliphatic-substituted phenylene group(s) may include straight-chained, non-aromatic ring, or branched aliphatic moieties, and may include saturated or un-saturated structures such as alkanes (e.g., paraffins), alkenes (e.g., olefins), and alkynes (e.g., acetylenes).

A fluid composition may include a single polyphenyl thioether molecule or a mixture of polyphenyl thioether molecules. In some embodiments, a mixture of polyphenyl thioether molecules may form a eutectic composition. According to further embodiments, a lens fluid composition may include a mixture of polyphenyl thioether molecule(s) and polyphenyl ether(s). A lens fluid composition may be clear or tinted.

According to various embodiments, a liquid lens fluid composition may include a polyphenyl ether molecule having from 2 to 7 aromatic rings, where the rings include ortho substitutions, meta substitutions, ortho and meta substitutions, or a combination of ortho, meta, and para substitutions. Inter-ring linkages may include sulfur or oxygen. The liquid lens fluid composition may be characterized by a refractive index over the visible spectrum (e.g., at approximately 589 nm) of at least 1.4, a freezing point of less than approximately −10° C., and a viscosity less than approximately 1000 cP at room temperature.

Features from any of the embodiments described herein may be used in combination with one another in accordance with the general principles described herein. These and other embodiments, features, and advantages will be more fully understood upon reading the following detailed description in conjunction with the accompanying drawings and claims.

Figure 3:
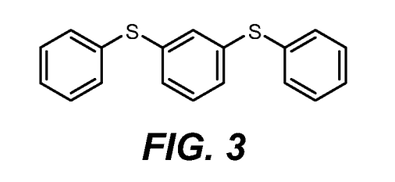
FIG. 3 is a schematic illustration of a linear, meta-linked polyphenyl thioether molecule according to various embodiments.
Figure 4:
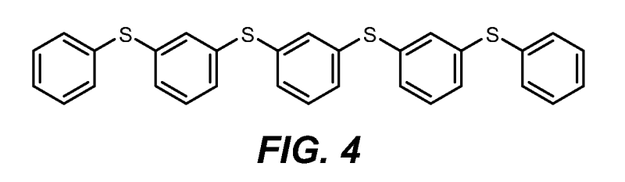
FIG. 4 is a schematic illustration of a linear, meta-linked polyphenyl thioether molecule according to some embodiments.
Figure 15:
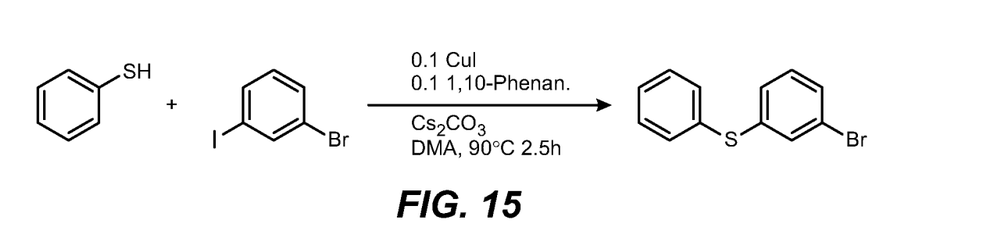
FIG. 15 depicts a synthesis route for preparing a (3-bromophenyl)(phenyl) sulfane intermediate compound according to some embodiments.
Figure 16:
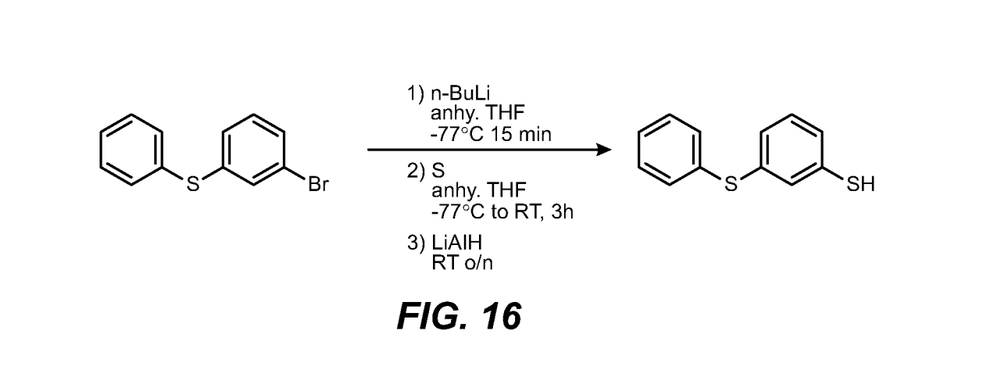
FIG. 16 depicts a synthesis route for preparing a 3-(phenylthio)benzenethiol intermediate compound from (3-bromophenyl)(phenyl) sulfane according to some embodiments.
Figure 17:
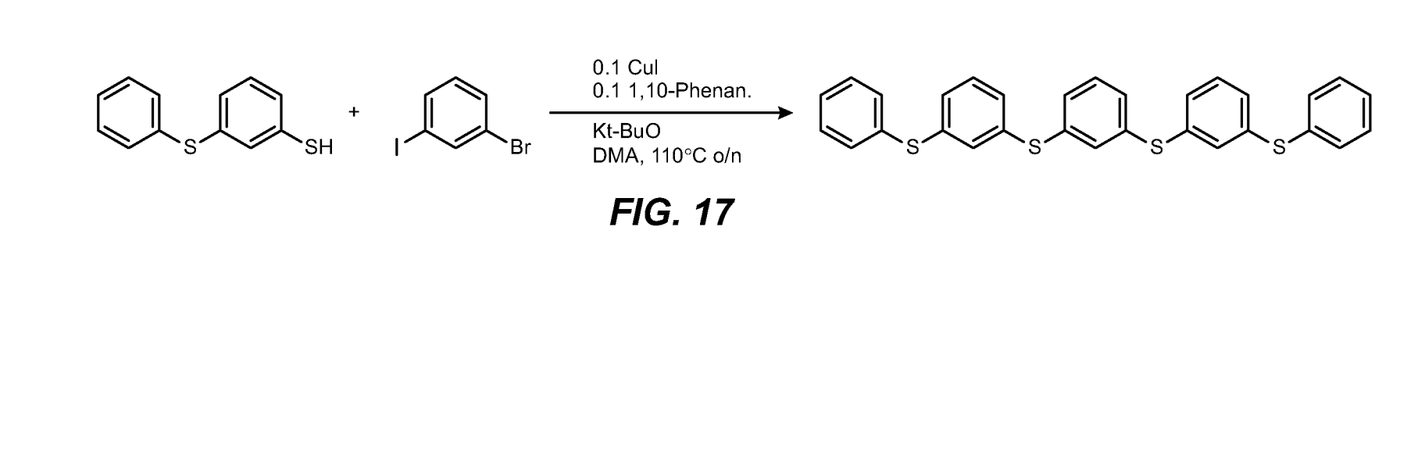
FIG. 17 shows an example synthesis path for preparing 1,3-bis((3-(phenylthio)phenyl)thio)benzene from 3-(phenylthio)benzenethiol according to some embodiments.

The following will provide, with reference to FIGS. 1-19, detailed descriptions of polyphenyl thioether-based liquid lens fluid compositions, liquid lenses, and apparatus incorporating liquid lenses that may include such fluid compositions. The discussion associated with FIGS. 1 and 2 includes a description of unactuated and actuated liquid lenses. The discussion associated with FIGS. 3-12 includes a description of example polyphenyl thioether molecules suitable for use as the lens fluid of a liquid lens. The discussion associated with FIG. 13 includes a description of a synthesis path for forming 1,3-bis(phenylthio)benzene, as shown in FIG. 3. The discussion associated with FIG. 14 includes a description of the rheological characteristics of 1,3-bis(phenylthio) benzene synthesized in accordance with a method disclosed herein. The discussion associate with FIGS. 15-17 includes a description of a multi-step synthesis path for forming 1,3-bis((3-(phenylthio)phenyl)thio)benzene, as shown in FIG. 4. The discussion associated with FIGS. 18 and 19 relates to exemplary augmented reality and virtual reality devices that may include a polyphenyl thioether-containing liquid lens.

Figure 1:
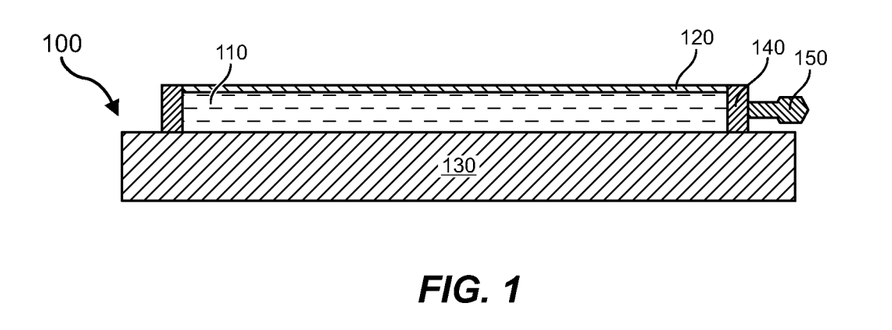
FIG. 1 is a schematic diagram of an exemplary liquid lens in an unactuated state according to some embodiments.

Referring to FIG. 1, illustrated is a cross-sectional view of an example variable focus lens, i.e., liquid lens. Liquid lens 100 may include a volume of lens fluid 110 disposed between a clear distensible membrane 120 and a clear planar substrate 130. An actuator 150 may be located at a position on peripheral seal 140 and may be operatively coupled to the lens 100 to apply a force to the lens fluid 110. In the embodiment of FIG. 1, the actuator 150 is in a neutral position where an upper surface of the membrane 120 is substantially planar.

Figure 2:
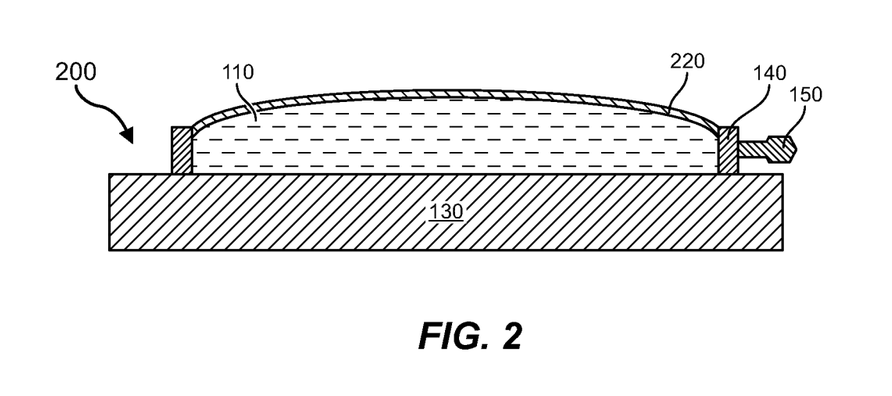
FIG. 2 is a schematic diagram of an exemplary liquid lens in an actuated state according to some embodiments.

Referring to FIG. 2, when the actuator 150 is driven to a second state, a compressive (tensile) stress may be applied to the lens fluid 110, which may cause the membrane 220 to bulge outwardly (inwardly) and form a convex (concave) shape opposite the substrate 130. Planar substrate 130 may include a transparent lens, for example. In unillustrated embodiments, as will be appreciated by those skilled in the art, planar substrate 130 may be replaced by a convex (e.g., plano-convex) lens or a concave (e.g., plano-concave) lens, although further lens architectures are contemplated.

According to certain embodiments, the lens fluid 110 and the membrane 120 may respectively include materials that are chemically repulsive to each other, such as, for example, hydrophilic and hydrophobic materials or oleophilic and oleophobic materials. For instance, the polyphenyl thioether compositions disclosed herein may be used as a lens fluid and may be oleophilic whereas the membrane 120, 220 of an associated liquid lens may include a oleophobic material or a material treated to have a oleophobic surface that is in contact with the lens fluid. A repulsive force between the lens fluid and the membrane can inhibit the absorption of the lens fluid into the membrane and/or prevent leaking of the lens fluid through the membrane.

Figure 5:
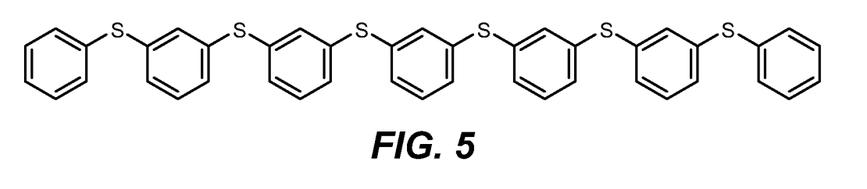
FIG. 5 is a schematic illustration of a linear, meta-linked polyphenyl thioether molecule according to further embodiments.

Referring to FIGS. 3-5, illustrated are example linear chain polyphenyl thioethers having three aromatic groups, five aromatic groups, and seven aromatic groups, respectively. In each illustrated structure, the aromatic groups are linked by thioether bonds. That is, the polyphenyl thioether molecules may contain all-sulfur linking of the phenyl and phenylene rings. Such polyphenyl thioether molecules may, in some examples, be characterized as consisting of sulfur linkages. In alternate embodiments, one or more sulfur linkages may be replaced by an oxygen linkage. In the structures of FIGS. 3-5, the phenylene rings are fully meta-substituted, though other substitution schemes are contemplated.

Figure 6:
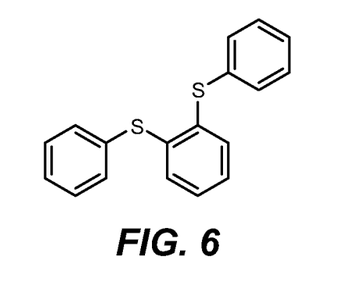
FIG. 6 shows an ortho-linked polyphenyl thioether molecule according to some embodiments.
Figure 7:
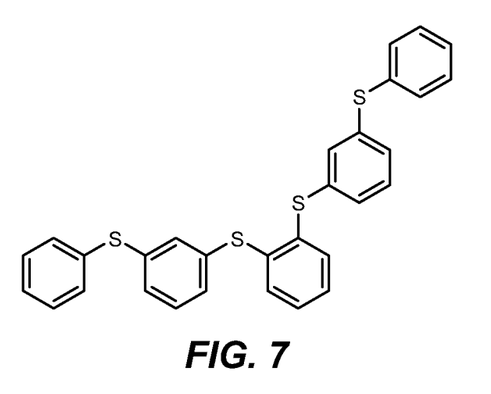
FIG. 7 shows an ortho- and meta-linked polyphenyl thioether molecule according to certain embodiments.
Figure 8:
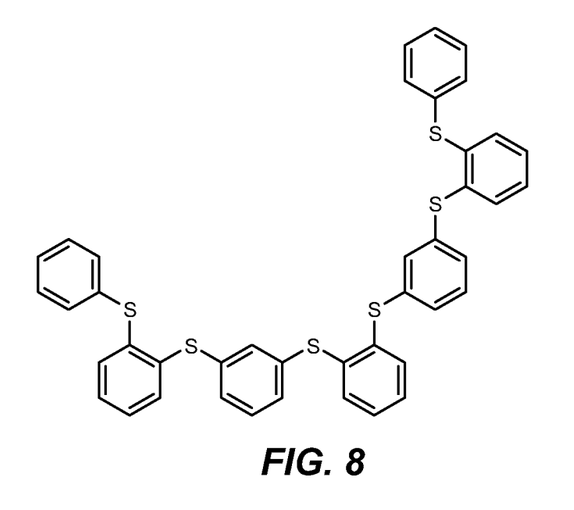
FIG. 8 shows an ortho- and meta-linked polyphenyl thioether molecule according to further embodiments.
Figure 9:
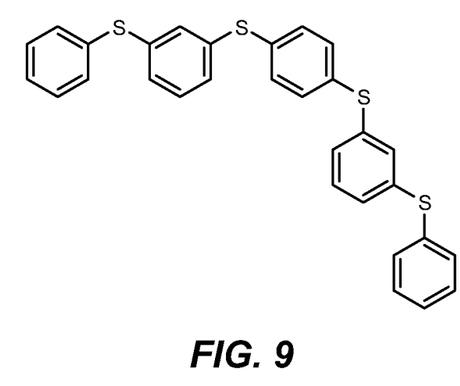
FIG. 9 shows a meta- and para-linked polyphenyl thioether molecule according to some embodiments.

Referring to FIG. 6, for example, illustrated is a linear chain polyphenyl thioether molecule having three aromatic groups where the phenylene group is ortho-substituted. Referring to FIG. 7 and FIG. 8, further example linear chain polyphenyl thioether molecules may include both ortho- and meta-substituted phenylene groups, whereas the polyphenyl thioether molecule illustrated in FIG. 9 may include both meta- and para-substituted phenylene groups.

Figure 10:
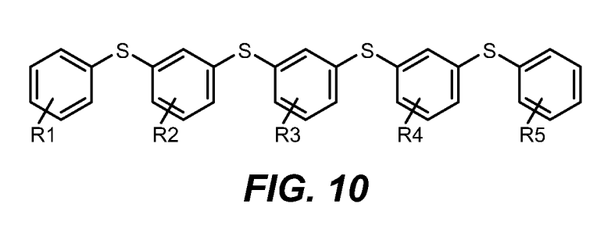
FIG. 10 shows a substituted meta-linked polyphenyl thioether molecule according to some embodiments.

According to further embodiments, a polyphenyl thioether molecule may be represented by the structure illustrated in FIG. 10, where each chemical group (R), i.e., R1, R2, R3, R4, and R5 may be independently selected from hydrogen, alkyl, haloalkyl, halogen, phenyl, alkaryl, hydroxyl, alkoxy, aralkyl, etc. Example chemical groups (e.g., R1, R2, R3, R4, R5) may include methyl, ethyl, hydroxyl, thiol, methoxy, thiomethyl, Br, Cl, I, and the like.

Figure 11:
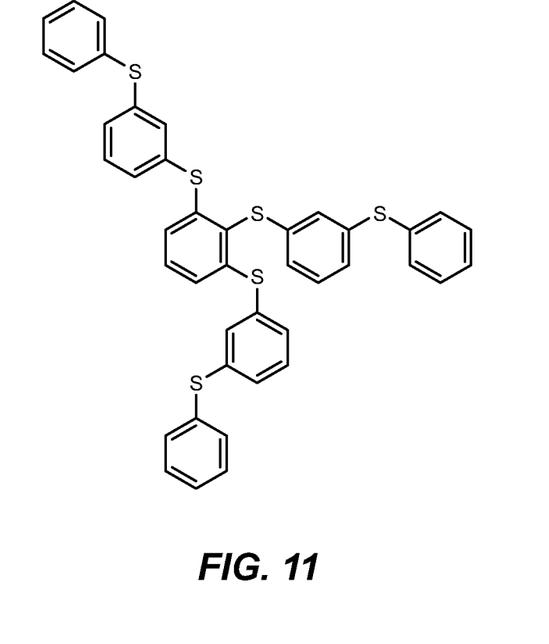
FIG. 11 shows a star-shaped polyphenyl thioether molecule according to some embodiments.
Figure 12:
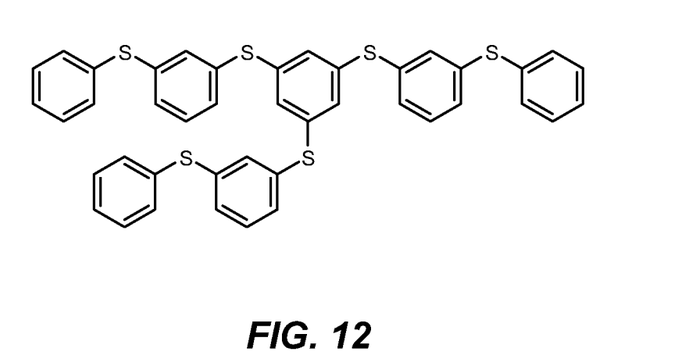
FIG. 12 shows a star-shaped polyphenyl thioether molecule according to further embodiments.
Figure 13:
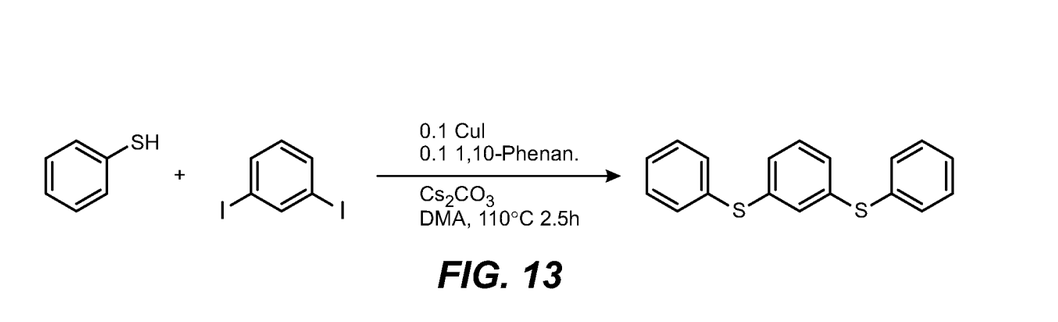
FIG. 13 depicts a synthesis path for preparing 1,3-bis(phenylthio)benzene according to some embodiments.

As will be appreciated, although the foregoing chemical group substitutions are illustrated in connection with a linear polyphenyl thioether molecule having five aromatic rings, such substitutions may be made in polyphenyl thioether molecules having a lesser or greater number of aromatic rings. Furthermore, one or more chemical groups (R), if provided, may be bonded to one or more phenyl or phenylene groups (P). Furthermore, a chemically substituted or un-substituted polyphenyl thioether molecule may be non-linear. Example non-linear, star-shaped polyphenyl thioether molecules are shown in FIG. 11 and FIG. 12.

Synthesis Trials

The following are examples of synthesis paths that may be used to form various polyphenyl thioether-based lens fluid compositions. For example, the synthesis of 1,3-bis (phenylthio)benzene, as shown in FIG. 3, is described with reference to Trial 1. A three-step process for preparing 1,3-bis((3-(phenylthio)phenyl)thio)benzene, as shown in FIG. 4, is described with reference to Trials 2-4.

Trial 1—Synthesis of 1,3-bis(phenylthio)benzene

Into a reaction vessel, 1,3-diiodobenzene (160 g) was added, followed by cesium carbonate (379.2 g), copper iodide (9.218 g), and 1,10-phenanthroline (1,10-Phenan.) (8.722 g). The vessel contents were then dissolved in dimethylacetamide (DMA), and thiophenol (PhSH) (106.654 g) was added and the mixture was heated to 120° C. The reaction was run at 120° C. overnight (o/n).

The reaction vessel was cooled to room temperature and quenched with water (1.5 L). The reaction product was diluted with petroleum ether (1.5 L) and stirred for 15 minutes prior to filtering with a diatomaceous earth adsorbent and washing with petroleum ether (1.5 L). The organic layers were combined and washed with saturated aqueous sodium thiosulfate (750 mL), water (750 mL), brine (1 L), and dried over magnesium sulfate and filtered. Activated charcoal was added to the petroleum ether solution and stirred at room temperature for 30 minutes. The activated charcoal was removed by filtration and the filtrate was concentrated to give the final product. Yield (133 g, 93.4%); $^1$H NMR (400 MHz, DMSO-d6) 7.38-7.31 (m, 11H), 7.15 (dd, J=7.9, 1.8 Hz, 2H), 7.02-7.01 (m, 1H); $^{13}$C NMR (100 MHz, DMSO-d6) 137.40, 133.31, 131.96, 130.51, 129.90, 129.82, 128.27, 128.05; LC/MS: 294.0 [M+Na]$^+$.

Figure 14:
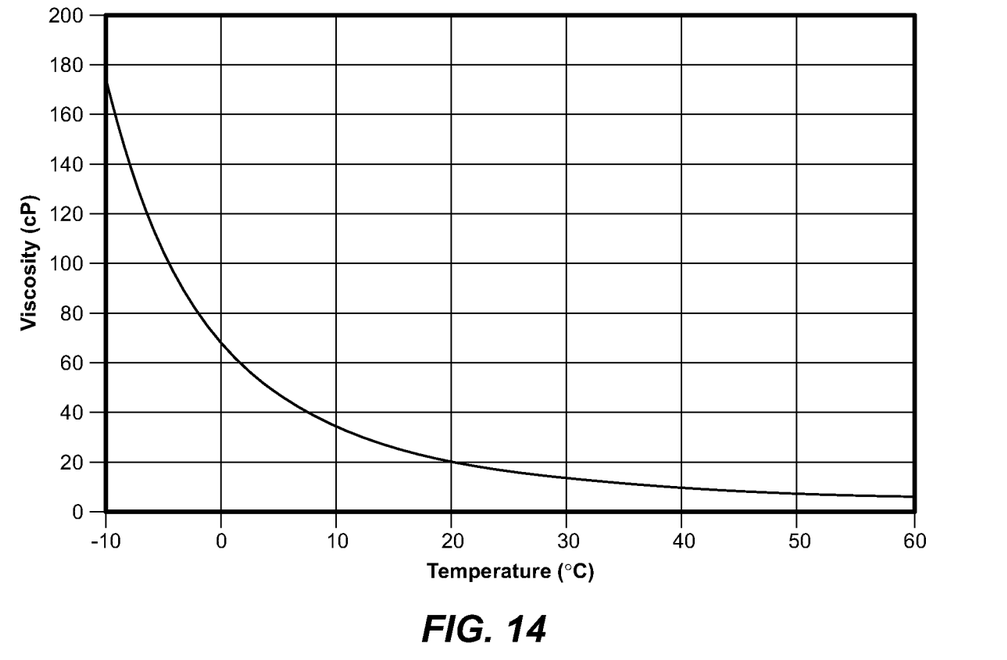
FIG. 14 shows the rheological characteristics of the polyphenyl thioether composition of FIG. 13 according to certain embodiments.

The reaction product of Trial 1 may be characterized as a light yellow liquid having a refractive index at 589 nm of approximately 1.67, a density of approximately 1.18 g/mL, and a freezing point of approximately −63° C. The Trial 1 synthesis is summarized in FIG. 13. A plot of viscosity versus temperature for the 1,3-bis(phenylthio)benzene of Trial 1 is shown in FIG. 14.

Trial 2A—(3-bromophenyl)(phenyl) sulfane—intermediate

Phenyl disulfide (0.290 g), copper (0.169 g), copper (I) iodide (0.422 g), and 1,10-phenanthroline (0.399 g) were added to a dry 3-neck 50 milliliter round bottom flask and placed under vacuum for 30 minutes. The reaction flask was then purged with nitrogen and 10 mL of N,N-dimethylacetamide was added, followed by 2.817 mL of 3-bromoiodobenzene. The flask contents were then heated to 100° C. for 16 h. The crude reaction mixture was washed once with saturated sodium bicarbonate solution, once with water, once with saturated sodium chloride solution, dried over magnesium sulfate and concentrated under reduced pressure. LC-MS: 296 [M+Na]$^+$.

Trial 2B—(3-bromophenyl)(phenyl) sulfane—intermediate (alternate route)

Cesium carbonate (34.536 g), 1,10-phenanthroline (1.931 g), and copper (I) iodide (2.016 g) were added to a round bottom flask and dissolved in dimethylacetamide (50 mL). Then 1-bromo-3-iodobenzene (14.253 g, 6.438 mL) and thiophenol (5.873 g, 5.474 mL) were added to the flask and the contents were heated to 90° C. for 2.5 h.

The reaction was then allowed to cool to room temperature and was quenched with 100 mL of water. The aqueous layer was washed 3 times with 100 mL diethyl ether. The organic layers were combined and washed once with saturated sodium bicarbonate solution, once with water, and once with saturated sodium chloride solution. The diethyl ether solution was dried over magnesium sulfate and concentrated with no further purification. Yield (13.005 g 95% pure by LC/MS [0.0491 mol, 97.2%]); $^1$H NMR (80 MHz, CDCl$_3$) 7.44-7.08 (m, 9H); $^{13}$C NMR (20 MHz, CDCl$_3$) 138.67, 132.46, 132.38, 130.50, 129.77, 129.60, 128.54, 128.08, 123.11; LC/MS: 286.0 [M+Na]$^+$. The Trial 2B synthesis of the (3-bromophenyl)(phenyl) sulfane intermediate compound is summarized in FIG. 15.

Trial 3—3-(phenylthio)benzenethiol—intermediate

In a first reaction vessel, (3-bromophenyl)(phenyl) sulfane (3 g from Trial 2B) was dissolved in anhydrous tetrahydrofuran (20 mL) and cooled to −77° C. in a dry ice/isopropyl alcohol bath. N-butyllithium was then added to the solution at −77° C. and allowed to react for 15 minutes. In a second reaction vessel, elemental sulfur (0.725 g) was added and dissolved in anhydrous tetrahydrofuran (10 mL) and cooled to −77° C. in a dry ice/isopropyl alcohol bath.

After 15 minutes, the contents of the first reaction vessel were cannulated into the second reaction vessel and the solution was reacted a −77° C. for 1 hour then allowed to warm to room temperature over 3 hours. The reaction was then cooled to 0° C. and lithium aluminum hydride (1.289 g) was added via solid addition funnel. The reaction was allowed to warm to room temperature and left to react overnight.

The reaction was quenched to 0° C. via the addition of isopropyl alcohol. Then 100 mL of water was added. The aqueous layer was extracted with ethyl acetate (3×20 mL). The organic layers were combined and washed once with saturated sodium bicarbonate solution, once with water, and once with saturated sodium chloride solution, and then dried over magnesium sulfate and concentrated.

The crude reaction mixture was purified via reverse phase column purification; 0 to 100% acetonitrile, 0.1% trifluoroacetic acid in water, 0.1% trifluoroacetic acid over 30 column volumes. Yield (0.649 g); $^1$H NMR (80 MHz, CDCl$_3$) 7.43-7.07 (m, 9H), 3.42 (s, 1H); $^{13}$C NMR (20 MHz, CDCl$_3$) 137.21, 131.92, 130.72, 129.77, 129.50, 127.72; LC/MS: 219.0 [M+H]$^+$. The Trial 3 synthesis of the 3-(phenylthio)benzenethiol intermediate compound is summarized in FIG. 16.

Trial 4—Synthesis of 1,3-bis((3-(phenylthio)phenyl)thio)benzene

Potassium tert-butoxide (0.555 g), 1,10-phenanthroline (0.1M, 0.27 g), copper (I) iodide (0.1M, 0.028 g) and 3-(phenylthio)benzenethiol (0.649 g from Trial 3) were added to a reaction vessel and then dissolved in dimethylacetamide (10 mL). 1-bromo-3-iodobenzene (0.420 g) was then added to the reaction vessel and the contents were heated to 110° C. overnight.

The reaction was then allowed to cool to room temperature, and 50 mL of water was added to the reaction vessel. The aqueous layer was then extracted with ethyl acetate (3×10 mL). The organic layers were combined and washed once with saturated sodium bicarbonate solution, once with water, once with saturated sodium chloride solution, and then dried over magnesium sulfate and concentrated.

The crude reaction mixture was purified via reverse phase column purification; 60 to 100% acetonitrile, 0.1% trifluoroacetic acid in water, 0.1% trifluoroacetic acid over 11 column volumes then 100% acetonitrile 0.1% trifluoroacetic acid for another 11 column volumes. Yield (0.120 g); $^1$H NMR (80 MHz, CDCl$_3$) 7.36-7.07 (m, 22H); LC/MS: 511.1 [M+H]$^+$. The Trial 4 synthesis of 1,3-bis((3-(phenylthio)phenyl)thio)benzene is summarized in FIG. 17.

Disclosed is a class of polyphenyl thioethers capable of being used as the fluid in a liquid lens. The polyphenyl thioethers are characterized by a high refractive index, low viscosity, and are non-toxic, enabling the production of a liquid lens that is thin, light, and comfortable to wear. The relatively large molecular weight of these polyphenyl thioethers may prevent their permeating the membrane of the liquid lens, which may achieve a variety of safety considerations. In one example, a polyphenyl thioether composition may contain 2-7 aromatic rings and a sulfur linkage between each of the aromatic rings. The aromatic rings can include all ortho-substitutions, all meta-substitutions, a combination of ortho-substitutions and meta-substitutions, or a combination of ortho-, meta-, and para-substitutions. In another example, the aromatic rings can include aliphatic structures or a halogen element. The polyphenyl thioether molecules may be linear, branched, or star shaped and may include a single polyphenyl thioether molecule, a blend of polyphenyl thioether molecules, or a blend of polyphenyl thioether(s) with polyphenyl ether(s).

EXAMPLE EMBODIMENTS

Example 1: A liquid lens fluid composition includes a polyphenyl ether molecule having from 2 to 7 aromatic rings, where the aromatic rings have ortho substitutions, meta substitutions, a combination of ortho and meta substitutions, or a combination of ortho, meta, and para substitutions, and one or more inter-ring linkages include sulfur.

Example 2: The liquid lens fluid composition of Example 1, where all the inter-ring linkages include sulfur.

Example 3: The liquid lens fluid composition of any of Examples 1 and 2, where the composition includes all ortho substitutions.

Example 4: The liquid lens fluid composition of any of Examples 1 and 2, where the composition includes all meta substitutions.

Example 5: The liquid lens fluid composition of any of Examples 1-4, characterized by a refractive index over the visible spectrum of at least approximately 1.4.

Example 6: The liquid lens fluid composition of any of Examples 1-5, characterized by a viscosity of less than approximately 1000 cP at 25° C. and a freezing point of less than approximately −10° C.

Example 7: The liquid lens fluid composition of any of Examples 1-6, where the polyphenyl ether molecule is substituted with an aliphatic group or a halogen element selected from chlorine, bromine, and iodine.

Example 8: A liquid lens fluid composition includes a polyphenyl thioether molecule having from 2 to 7 aromatic rings, where all the rings include either ortho substitutions or meta substitutions.

Example 9: The liquid lens fluid composition of Example 8, where the composition includes only ortho substitutions.

Example 10: The liquid lens fluid composition of Example 8, where the composition includes only meta substitutions.

Example 11: The liquid lens fluid composition of any of Examples 8-10, characterized by a refractive index over the visible spectrum of at least approximately 1.4.

Example 12: The liquid lens fluid composition of any of Examples 8-11, characterized by a viscosity of less than approximately 1000 cP at 25° C. and a freezing point of less than approximately −10° C.

Example 13: The liquid lens fluid composition of any of Examples 8-12, where the polyphenyl thioether molecule is substituted with an aliphatic group or a halogen element selected from chlorine, bromine, and iodine.

Example 14: A variable focus lens includes a transparent wall member, a transparent distensible membrane located over at least a portion of the transparent wall member, and a layer of a liquid lens fluid composition located between the wall member and the distensible membrane, where the liquid lens fluid composition comprises a polyphenyl ether molecule having from 2 to 7 aromatic rings, the rings having ortho substitutions, meta substitutions, a combination of ortho and meta substitutions, or a combination of ortho, meta, and para substitutions.

Example 15: The variable focus lens of Example 14, where the distensible membrane includes an oleophobic surface facing the liquid lens fluid and the liquid lens fluid is oleophilic.

Example 16: The variable focus lens of any of Examples 14 and 15, where the composition includes only ortho substitutions.

Example 17: The variable focus lens of any of Examples 14 and 15, where the composition includes only meta substitutions.

Example 18: The variable focus lens of any of Examples 14-17, where the polyphenyl ether molecule is substituted with an aliphatic group or a halogen element selected from chlorine, bromine, and iodine.

Example 19: The variable focus lens of any of Examples 14-18, where the liquid lens fluid composition includes a polyphenyl thioether.

Example 20: The variable focus lens of any of Examples 14-19, where the liquid lens fluid is characterized by a refractive index over the visible spectrum of at least approximately 1.4, a viscosity of less than approximately 1000 cP at 25° C., and a freezing point of less than approximately −10° C.

Embodiments of the present disclosure may include or be implemented in conjunction with various types of artificial reality systems. Artificial reality is a form of reality that has been adjusted in some manner before presentation to a user, which may include, for example, a virtual reality, an augmented reality, a mixed reality, a hybrid reality, or some combination and/or derivative thereof. Artificial reality content may include completely computer-generated content or computer-generated content combined with captured (e.g., real-world) content. The artificial reality content may include video, audio, haptic feedback, or some combination thereof, any of which may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, for example, create content in an artificial reality and/or are otherwise used in (e.g., to perform activities in) an artificial reality.

Artificial reality systems may be implemented in a variety of different form factors and configurations. Some artificial reality systems may be designed to work without near-eye displays (NEDs). Other artificial reality systems may include an NED that also provides visibility into the real world (e.g., augmented reality system 1800 in FIG. 18) or that visually immerses a user in an artificial reality (e.g., virtual reality system 1900 in FIG. 19). While some artificial reality devices may be self-contained systems, other artificial reality devices may communicate and/or coordinate with external devices to provide an artificial reality experience to a user. Examples of such external devices include handheld controllers, mobile devices, desktop computers, devices worn by a user, devices worn by one or more other users, and/or any other suitable external system.

Figure 18:
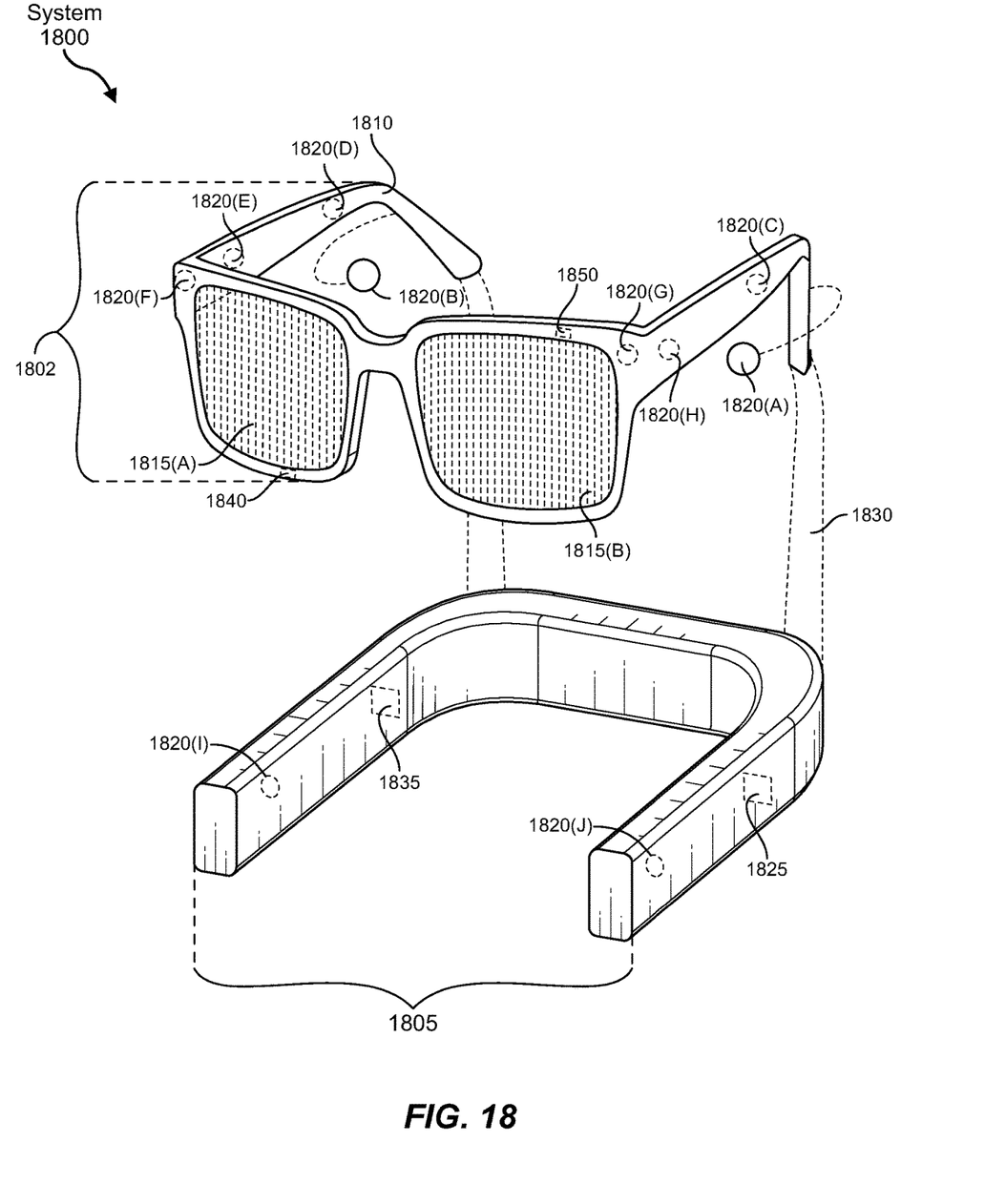
FIG. 18 is an illustration of exemplary augmented reality glasses that may be used in connection with embodiments of this disclosure.

Turning to FIG. 18, augmented reality system 1800 may include an eyewear device 1802 with a frame 1810 configured to hold a left display device 1815(A) and a right display device 1815(B) in front of a user's eyes. Display devices 1815(A) and 1815(B) may act together or independently to present an image or series of images to a user. While augmented reality system 1800 includes two displays, embodiments of this disclosure may be implemented in augmented reality systems with a single NED or more than two NEDs.

In some embodiments, augmented reality system 1800 may include one or more sensors, such as sensor 1840. Sensor 1840 may generate measurement signals in response to motion of augmented reality system 1800 and may be located on substantially any portion of frame 1810. Sensor 1840 may represent a position sensor, an inertial measurement unit (IMU), a depth camera assembly, a structured light emitter and/or detector, or any combination thereof. In some embodiments, augmented reality system 1800 may or may not include sensor 1840 or may include more than one sensor. In embodiments in which sensor 1840 includes an IMU, the IMU may generate calibration data based on measurement signals from sensor 1840. Examples of sensor 1840 may include, without limitation, accelerometers, gyroscopes, magnetometers, other suitable types of sensors that detect motion, sensors used for error correction of the IMU, or some combination thereof.

Augmented reality system 1800 may also include a microphone array with a plurality of acoustic transducers 1820 (A)-1820(J), referred to collectively as acoustic transducers 1820. Acoustic transducers 1820 may be transducers that detect air pressure variations induced by sound waves. Each acoustic transducer 1820 may be configured to detect sound and convert the detected sound into an electronic format (e.g., an analog or digital format). The microphone array in FIG. 18 may include, for example, ten acoustic transducers: 1820(A) and 1820(B), which may be designed to be placed inside a corresponding ear of the user, acoustic transducers 1820(C), 1820(D), 1820(E), 1820(F), 1820(G), and 1820 (H), which may be positioned at various locations on frame 1810, and/or acoustic transducers 1820(1) and 1820(J), which may be positioned on a corresponding neckband 1805.

In some embodiments, one or more of acoustic transducers 1820(A)-(F) may be used as output transducers (e.g., speakers). For example, acoustic transducers 1820(A) and/ or 1820(B) may be earbuds or any other suitable type of headphone or speaker.

The configuration of acoustic transducers 1820 of the microphone array may vary. While augmented reality system 1800 is shown in FIG. 18 as having ten acoustic transducers 1820, the number of acoustic transducers 1820 may be greater or less than ten. In some embodiments, using higher numbers of acoustic transducers 1820 may increase the amount of audio information collected and/or the sensitivity and accuracy of the audio information. In contrast, using a lower number of acoustic transducers 1820 may decrease the computing power required by an associated controller 1850 to process the collected audio information. In addition, the position of each acoustic transducer 1820 of the microphone array may vary. For example, the position of an acoustic transducer 1820 may include a defined position on the user, a defined coordinate on frame 1810, an orientation associated with each acoustic transducer 1820, or some combination thereof.

Acoustic transducers 1820(A) and 1820(B) may be positioned on different parts of the user's ear, such as behind the pinna, behind the tragus, and/or within the auricle or fossa. Or, there may be additional acoustic transducers 1820 on or surrounding the ear in addition to acoustic transducers 1820 inside the ear canal. Having an acoustic transducer 1820 positioned next to an ear canal of a user may enable the microphone array to collect information on how sounds arrive at the ear canal. By positioning at least two of acoustic transducers 1820 on either side of a user's head (e.g., as binaural microphones), augmented reality device 1800 may simulate binaural hearing and capture a 3D stereo sound field around about a user's head. In some embodiments, acoustic transducers 1820(A) and 1820(B) may be connected to augmented reality system 1800 via a wired connection 1830, and in other embodiments acoustic transducers 1820(A) and 1820(B) may be connected to augmented reality system 1800 via a wireless connection (e.g., a Bluetooth connection). In still other embodiments, acoustic transducers 1820(A) and 1820(B) may not be used at all in conjunction with augmented reality system 1800.

Acoustic transducers 1820 on frame 1810 may be positioned along the length of the temples, across the bridge, above or below display devices 1815(A) and 1815(B), or some combination thereof. Acoustic transducers 1820 may be oriented such that the microphone array is able to detect sounds in a wide range of directions surrounding the user wearing the augmented reality system 1800. In some embodiments, an optimization process may be performed during manufacturing of augmented reality system 1800 to determine relative positioning of each acoustic transducer 1820 in the microphone array.

In some examples, augmented reality system 1800 may include or be connected to an external device (e.g., a paired device), such as neckband 1805. Neckband 1805 generally represents any type or form of paired device. Thus, the following discussion of neckband 1805 may also apply to various other paired devices, such as charging cases, smart watches, smart phones, wrist bands, other wearable devices, hand-held controllers, tablet computers, laptop computers, other external compute devices, etc.

As shown, neckband 1805 may be coupled to eyewear device 1802 via one or more connectors. The connectors may be wired or wireless and may include electrical and/or non-electrical (e.g., structural) components. In some cases, eyewear device 1802 and neckband 1805 may operate independently without any wired or wireless connection between them. While FIG. 18 illustrates the components of eyewear device 1802 and neckband 1805 in example locations on eyewear device 1802 and neckband 1805, the components may be located elsewhere and/or distributed differently on eyewear device 1802 and/or neckband 1805. In some embodiments, the components of eyewear device 1802 and neckband 1805 may be located on one or more additional peripheral devices paired with eyewear device 1802, neckband 1805, or some combination thereof.

Pairing external devices, such as neckband 1805, with augmented reality eyewear devices may enable the eyewear devices to achieve the form factor of a pair of glasses while still providing sufficient battery and computation power for expanded capabilities. Some or all of the battery power, computational resources, and/or additional features of augmented reality system 1800 may be provided by a paired device or shared between a paired device and an eyewear device, thus reducing the weight, heat profile, and form factor of the eyewear device overall while still retaining desired functionality. For example, neckband 1805 may allow components that would otherwise be included on an eyewear device to be included in neckband 1805 since users may tolerate a heavier weight load on their shoulders than they would tolerate on their heads. Neckband 1805 may also have a larger surface area over which to diffuse and disperse heat to the ambient environment. Thus, neckband 1805 may allow for greater battery and computation capacity than might otherwise have been possible on a stand-alone eyewear device. Since weight carried in neckband 1805 may be less invasive to a user than weight carried in eyewear device 1802, a user may tolerate wearing a lighter eyewear device and carrying or wearing the paired device for greater lengths of time than a user would tolerate wearing a heavy stand-alone eyewear device, thereby enabling users to more fully incorporate artificial reality environments into their day-to-day activities.

Neckband 1805 may be communicatively coupled with eyewear device 1802 and/or to other devices. These other devices may provide certain functions (e.g., tracking, localizing, depth mapping, processing, storage, etc.) to augmented reality system 1800. In the embodiment of FIG. 18, neckband 1805 may include two acoustic transducers (e.g., 1820(1) and 1820(J)) that are part of the microphone array (or potentially form their own microphone subarray). Neckband 1805 may also include a controller 1825 and a power source 1835.

Acoustic transducers 1820(1) and 1820(J) of neckband 1805 may be configured to detect sound and convert the detected sound into an electronic format (analog or digital). In the embodiment of FIG. 18, acoustic transducers 1820(1) and 1820(J) may be positioned on neckband 1805, thereby increasing the distance between the neckband acoustic transducers 1820(1) and 1820(J) and other acoustic transducers 1820 positioned on eyewear device 1802. In some cases, increasing the distance between acoustic transducers 1820 of the microphone array may improve the accuracy of beamforming performed via the microphone array. For example, if a sound is detected by acoustic transducers 1820(C) and 1820(D) and the distance between acoustic transducers 1820(C) and 1820(D) is greater than, e.g., the distance between acoustic transducers 1820(D) and 1820(E), the determined source location of the detected sound may be more accurate than if the sound had been detected by acoustic transducers 1820(D) and 1820(E).

Controller 1825 of neckband 1805 may process information generated by the sensors on neckband 1805 and/or augmented reality system 1800. For example, controller 1825 may process information from the microphone array that describes sounds detected by the microphone array. For each detected sound, controller 1825 may perform a direction-of-arrival (DOA) estimation to estimate a direction from which the detected sound arrived at the microphone array. As the microphone array detects sounds, controller 1825 may populate an audio data set with the information. In embodiments in which augmented reality system 1800 includes an inertial measurement unit, controller 1825 may compute all inertial and spatial calculations from the IMU located on eyewear device 1802. A connector may convey information between augmented reality system 1800 and neckband 1805 and between augmented reality system 1800 and controller 1825. The information may be in the form of optical data, electrical data, wireless data, or any other transmittable data form. Moving the processing of information generated by augmented reality system 1800 to neckband 1805 may reduce weight and heat in eyewear device 1802, making it more comfortable to the user.

Power source 1835 in neckband 1805 may provide power to eyewear device 1802 and/or to neckband 1805. Power source 1835 may include, without limitation, lithium ion batteries, lithium-polymer batteries, primary lithium batteries, alkaline batteries, or any other form of power storage. In some cases, power source 1835 may be a wired power source. Including power source 1835 on neckband 1805 instead of on eyewear device 1802 may help better distribute the weight and heat generated by power source 1835.

As noted, some artificial reality systems may, instead of blending an artificial reality with actual reality, substantially replace one or more of a user's sensory perceptions of the real world with a virtual experience. One example of this type of system is a head-worn display system, such as virtual reality system 1900 in FIG. 19, that mostly or completely covers a user's field of view. Virtual reality system 1900 may include a front rigid body 1902 and a band 1904 shaped to fit around a user's head. Virtual reality system 1900 may also include output audio transducers 1906(A) and 1906(B). Furthermore, while not shown in FIG. 19, front rigid body 1902 may include one or more electronic elements, including one or more electronic displays, one or more inertial measurement units (IMUs), one or more tracking emitters or detectors, and/or any other suitable device or system for creating an artificial reality experience.

Figure 19:
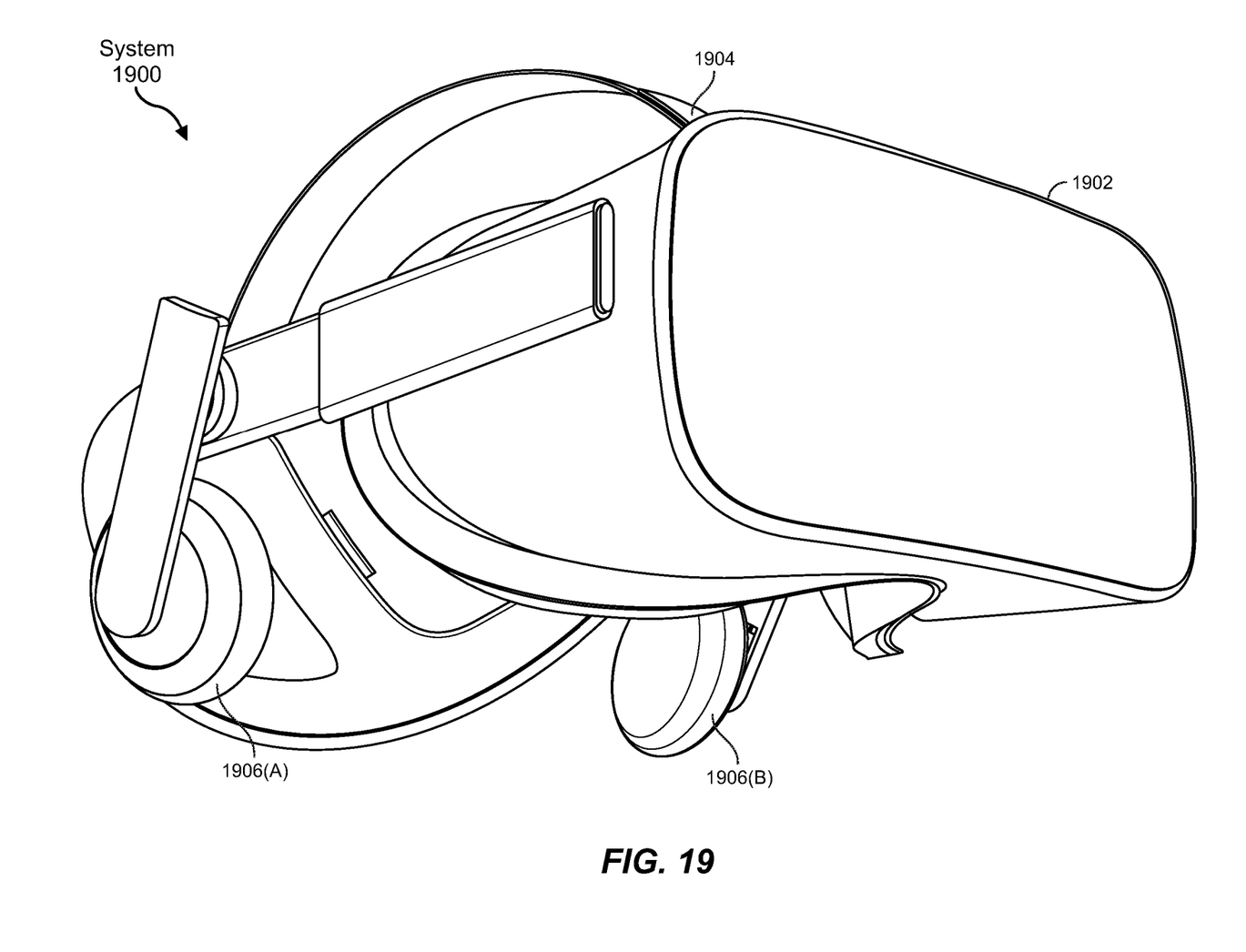
FIG. 19 is an illustration of an exemplary virtual reality headset that may be used in connection with embodiments of this disclosure.

Artificial reality systems may include a variety of types of visual feedback mechanisms. For example, display devices in augmented reality system 1800 and/or virtual reality system 1900 may include one or more liquid crystal displays (LCDs), light emitting diode (LED) displays, organic LED (OLED) displays, digital light project (DLP) micro-displays, liquid crystal on silicon (LCoS) micro-displays, and/or any other suitable type of display screen. Artificial reality systems may include a single display screen for both eyes or may provide a display screen for each eye, which may allow for additional flexibility for varifocal adjustments or for correcting a user's refractive error. Some artificial reality systems may also include optical subsystems having one or more lenses (e.g., conventional concave or convex lenses, Fresnel lenses, adjustable liquid lenses, etc.) through which a user may view a display screen. A liquid lens may include a polyphenyl thioether-based lens fluid as disclosed herein. These optical subsystems may serve a variety of purposes, including to collimate (e.g., make an object appear at a greater distance than its physical distance), to magnify (e.g., make an object appear larger than its actual size), and/or to relay (to, e.g., the viewer's eyes) light. These optical subsystems may be used in a non-pupil-forming architecture (such as a single lens configuration that directly collimates light but results in so-called pincushion distortion) and/or a pupil-forming architecture (such as a multi-lens configuration that produces so-called barrel distortion to nullify pincushion distortion).

In addition to or instead of using display screens, some artificial reality systems may include one or more projection systems. For example, display devices in augmented reality system 1800 and/or virtual reality system 1900 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial reality content and the real world. The display devices may accomplish this using any of a variety of different optical components, including waveguide components (e.g., holographic, planar, diffractive, polarized, and/or reflective waveguide elements), light-manipulation surfaces and elements (such as diffractive, reflective, and refractive elements and gratings), coupling elements, etc. Artificial reality systems may also be configured with any other suitable type or form of image projection system, such as retinal projectors used in virtual retina displays.

Artificial reality systems may also include various types of computer vision components and subsystems. For example, augmented reality system 1800 and/or virtual reality system 1900 may include one or more optical sensors, such as two-dimensional (2D) or 3D cameras, structured light transmitters and detectors, time-of-flight depth sensors, single-beam or sweeping laser rangefinders, 3D LiDAR sensors, and/or any other suitable type or form of optical sensor. An artificial reality system may process data from one or more of these sensors to identify a location of a user, to map the real world, to provide a user with context about real-world surroundings, and/or to perform a variety of other functions.

Artificial reality systems may also include one or more input and/or output audio transducers. In the examples shown in FIG. 19, output audio transducers 1906(A) and 1906(B) may include voice coil speakers, ribbon speakers, electrostatic speakers, piezoelectric speakers, bone conduction transducers, cartilage conduction transducers, tragus-vibration transducers, and/or any other suitable type or form of audio transducer. Similarly, input audio transducers may include condenser microphones, dynamic microphones, ribbon microphones, and/or any other type or form of input transducer. In some embodiments, a single transducer may be used for both audio input and audio output.

While not shown in FIG. 18, artificial reality systems may include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial reality devices, within other artificial reality devices, and/or in conjunction with other artificial reality devices.

By providing haptic sensations, audible content, and/or visual content, artificial reality systems may create an entire virtual experience or enhance a user's real-world experience in a variety of contexts and environments. For instance, artificial reality systems may assist or extend a user's perception, memory, or cognition within a particular environment. Some systems may enhance a user's interactions with other people in the real world or may enable more immersive interactions with other people in a virtual world. Artificial reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visual aids, etc.). The embodiments disclosed herein may enable or enhance a user's artificial reality experience in one or more of these contexts and environments and/or in other contexts and environments.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

It will be understood that when an element such as a layer or a region is referred to as being formed on, deposited on, or disposed "on" or "over" another element, it may be located directly on at least a portion of the other element, or one or more intervening elements may also be present. In contrast, when an element is referred to as being "directly on" or "directly over" another element, it may be located on at least a portion of the other element, with no intervening elements present.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a polyphenyl thioether fluid composition that comprises or includes meta-linkages include embodiments where a polyphenyl thioether fluid composition consists essentially of meta-linkages and embodiments where a polyphenyl thioether fluid composition consists of meta-linkages.

What is claimed is:

1. A liquid lens fluid composition comprising:
a polyphenyl ether molecule having from 2 to 7 aromatic rings, wherein the aromatic rings comprise ortho substitutions, meta substitutions, a combination of ortho and meta substitutions, or a combination of ortho, meta, and para substitutions, and one or more inter-ring linkages comprise sulfur.

2. The liquid lens fluid composition of claim 1, wherein all the inter-ring linkages comprise sulfur.

3. The liquid lens fluid composition of claim 1, wherein the composition consists essentially of ortho substitutions.

4. The liquid lens fluid composition of claim 1, wherein the composition consists essentially of meta substitutions.

5. The liquid lens fluid composition of claim 1, characterized by a refractive index over the visible spectrum of at least approximately 1.4.

6. The liquid lens fluid composition of claim 1, characterized by a viscosity of less than approximately 1000 cP at 25° C. and a freezing point of less than approximately −10° C.

7. The liquid lens fluid composition of claim 1, wherein the polyphenyl ether molecule is substituted with an aliphatic group or a halogen element selected from the group consisting of chlorine, bromine, and iodine.

8. A liquid lens fluid composition comprising:
a polyphenyl thioether molecule having from 2 to 7 aromatic rings, wherein all the rings comprise ortho substitutions or meta substitutions.

9. The liquid lens fluid composition of claim 8, wherein the composition consists essentially of ortho substitutions.

10. The liquid lens fluid composition of claim 8, wherein the composition consists essentially of meta substitutions.

11. The liquid lens fluid composition of claim 8, characterized by a refractive index over the visible spectrum of at least approximately 1.4.

12. The liquid lens fluid composition of claim 8, characterized by a viscosity of less than approximately 1000 cP at 25° C. and a freezing point of less than approximately −10° C.

13. The liquid lens fluid composition of claim 8, wherein the polyphenyl thioether molecule is substituted with an aliphatic group or a halogen element selected from the group consisting of chlorine, bromine, and iodine.

14. A variable focus lens comprising:
a transparent wall member;
a transparent distensible membrane located over at least a portion of the transparent wall member; and
a layer of a liquid lens fluid composition located between the wall member and the distensible membrane, wherein the liquid lens fluid composition comprises a polyphenyl ether molecule having from 2 to 7 aromatic rings, the rings having ortho substitutions, meta substitutions, a combination of ortho and meta substitutions, or a combination of ortho, meta, and para substitutions.

15. The variable focus lens of claim 14, wherein the distensible membrane comprises a oleophobic surface facing the liquid lens fluid and the liquid lens fluid is oleophilic.

16. The variable focus lens of claim 14, wherein the composition consists essentially of ortho substitutions.

17. The variable focus lens of claim 14, wherein the composition consists essentially of meta substitutions.

18. The variable focus lens of claim 14, wherein the polyphenyl ether molecule is substituted with an aliphatic group or a halogen element selected from the group consisting of chlorine, bromine, and iodine.

19. The variable focus lens of claim 14, wherein the liquid lens fluid composition comprises a polyphenyl thioether molecule.

20. The variable focus lens of claim 14, wherein the liquid lens fluid is characterized by a refractive index over the visible spectrum of at least approximately 1.4, a viscosity of less than approximately 1000 cP at 25° C., and a freezing point of less than approximately −10° C.

* * * * *